United States Patent [19]

Huber

[11] 4,230,665
[45] Oct. 28, 1980

[54] APPARATUS FOR AUTOMATICALLY GENERATING AND MEASURING GASEOUS MEASURING SAMPLES FROM A SERIES OF LIQUID SAMPLES

[75] Inventor: Bernhard W. Huber, Überlingen, Fed. Rep. of Germany

[73] Assignee: Bodenseewerk Perkin-Elmer & Co., GmbH, Überlingen, Fed. Rep. of Germany

[21] Appl. No.: 917,829

[22] Filed: Jun. 22, 1978

[30] Foreign Application Priority Data

Jul. 1, 1977 [DE] Fed. Rep. of Germany ....... 2729744

[51] Int. Cl.³ ................. G01N 27/66; G01N 21/13; G01N 33/20
[52] U.S. Cl. .................. 422/64; 73/423 A; 141/130; 422/80; 422/116; 23/230 R
[58] Field of Search ............ 422/63, 64, 65, 67, 422/68, 81, 116; 73/423 A; 141/130; 137/624.18, 624.2

[56] References Cited
U.S. PATENT DOCUMENTS

| | | | |
|---|---|---|---|
| 3,478,598 | 11/1969 | Nielson | 73/423 A |
| 3,726,144 | 4/1973 | Klein | 73/423 A |
| 3,881,872 | 5/1975 | Naono | 422/64 |
| 3,929,411 | 12/1975 | Takano et al. | 422/63 |
| 3,948,607 | 4/1976 | Atwood | 422/63 |
| 4,018,565 | 4/1977 | Fletcher et al. | 422/81 X |
| 4,090,848 | 5/1978 | Naono | 422/81 |
| 4,111,051 | 9/1978 | Tamm et al. | 73/423 A |

*Primary Examiner*—Michael S. Marcus
*Attorney, Agent, or Firm*—Salvatore A. Giarratana; Francis L. Masselle; Edwin T. Grimes

[57] ABSTRACT

Gaseous measuring samples like element hydrides are generated from liquid samples by reacting the same with reducing reagents in a reactor. In the reactor a countercurrent of inert gas strips the volatile reduction products from the reactor to convey the products to the measuring cell of an analytical measuring instrument. Various embodiments of the apparatus automatically controlling the supply of liquid sample and reagents to the reactor are disclosed such as mechanically or pneumatically controlled pumps. In each measuring cycle the reactor and respective components are washed to prevent contamination of succeeding samples; also, analytical determination of blank values as well as reference values can be included in each measuring cycle.

16 Claims, 9 Drawing Figures

APPARATUS FOR AUTOMATICALLY GENERATING AND MEASURING GASEOUS MEASURING SAMPLES FROM A SERIES OF LIQUID SAMPLES

BACKGROUND AND SUMMARY OF THE INVENTION

The invention relates to a method for automatically measuring the atomic absorption of gaseous measuring samples generated successively from a series of liquid samples, in which method within one measuring cycle a proportionate amount of liquid sample is supplied to a reactor through a sample input for reaction therein with proportionate amounts of at least two liquid reagents to form said gasous measuring sample which is conveyed to the measuring cell of an atomic absorption spectrometer by means of a carrier gas stream passing through said reactor.

The invention also relates to apparatus for carrying out the aforementioned method and comprising a reactor with carrier gas input and outlet lines, with a sample input and with at least two reagent inputs, sample taking means and supply means adapted to supply liquid sample and at least two liquid reagents to said reactor, and a heatable measuring cell placed in the optical path of rays of an atomic absorption spectrometer and connected to the reactor through the inert gas outlet line.

Methods and apparatus of such kind for the automatic determination of arsenic, antimony, or selenium in liquid samples known (P. D. Goulden, P. Brooksbank, Analytical Chemistry, Vol. 46, No. 11, Sept. 1974, pages 1431 to 1436; F. D. Pierce, T. C. Lamoreaux, H. R. Brown, R. S. Fraser, Applied Spectroscopy, Vol. 30, No. 1, 1976; pages 38 to 42). According to said known methods liquid sample and liquid reagents consisting of an aqueous acid on the one hand and either of an aqueous solution of sodium borohydride or an aluminum slurry on the other hand are fed by means of a multiple proportionating pump to a reactor in which the liquids are mixed and reacted chemically. The reactor is provided with input and output lines for inert gas which passes through the reaction mixture and serves as a carrier gas for the volatile hydrides formed in the reactor. The reactor is connected to a heatable stripping device in which the reaction mixture and the hydride containing inert gas are separated. Subsequently, the inert gas stream containing the hydride passes through a wash column and then enters a heatable tube placed in the optical path of rays of an atomic absorption spectrometer. The tube is heated to such a temperature that the gaseous hydride contained in the inert gas stream is decomposed to form atoms of the respective element to be determined by measuring the atomic absorption thereof.

In the known apparatus a separate device for taking samples of the liquid to be investigated ensures that no carry-over of material occurs between different samples. The whole apparatus and the method, however, are designed in such a way that mutual contamination of the liquid samples and of the gasous measuring samples cannot be exluded to the desired degree of perfection. The flow conduits and the apparatus components are of such size that only relatively large amounts of liquid samples will ensure that perfection which perfection is not obtained if smaller amounts of liquid sample are used.

One object to be achieved by the invention, therefore, is to provide a method and apparatus of the initially mentioned kind which are also suited for processing small amounts of liquid sample.

A further object to be achieved by the invention is to provide an apparatus of the initially mentioned kind having small-sized receptacles and flow conduits to enable the processing of small amounts of liquid sample, for example similar to those provided in clinical investigations.

A still further object to be achieved by the invention is to design the aforementioned method and apparatus in such a way that blank and reference measurements can also be taken without any further modifications.

According to the method of the invention the foregoing and other objects are achieved by feeding uniformly and continuously liquid reagents to the reactor during a first and a second time period of the measuring cycle and liquid sample during the second time period, both in countercurrent to a carrier gas stream, and by emptying and washing the reactor during a third through a sixth time period of the measuring cycle. During the first time period a blank sample may be supplied uniformly and continuously to the reactor at the same flow rate as the liquid sample is supplied during the second time period to conduct the blank measurement.

To perform the washing, wash liquid may be taken from a wash liquid receptacle during the third time period of the measuring cycle and supplied to the reactor through the sample input during a fourth time period.

The time periods of the measuring cycle may be of the same duration.

Since the different liquids are supplied in appropriate but over different time intervals small amounts of liquid sample can also be processed with sufficient safety and assurance against carry-over. Further, by washing the reactor the occurrence of mutual contamination of the gasous measuring samples originating from different liquid samples is prevented. Countercurrent flow of the inert gas with respect to the reaction mixture in the reactor will effect particularly efficient and complete removal of the gasous measuring sample from the reaction mixture immediately after formation without requiring a separate stripping device. Separate supply of the liquid reagents to the reactor also enables a blank measurement to be regularly taken before sample each measurement. This is of particular importance in the field of trace analysis.

In the method according to the invention, an addition liquid is fed uniformly and continuously to the reactor during further discrete time periods of the measuring cycle extended by said further time periods intermediate the second and the third time period thereof, while liquid reagents are being supplied to the reactor during said first and said second time period and during said further time periods. Said further time periods maybe of equal duration between themselves and of the same duration as the time periods of the measuring cycle.

The method according to the invention will thus enable blank and reference values to be taken for each respective liquid sample. The type of method used, again, will ensure that no carry-over occurs and that satisfying blank and reference values are obtained without large volumes of blank and reference samples being required.

In the case of gaseous measuring samples like mercury vapour the atomic absorption of which can be measured without applying thermal decomposition, the method in accordance with the invention is conducted in such a way that the flow of inert gas is interrupted before the second time period begins, the gas mixture enclosed in the reactor and the measuring cell being circulated in a closed loop during the second and third time period.

The aforementioned objects are achieved by an apparatus according to the invention comprising a reactor in the form of a reaction vessel with a packing, the reaction vessel having an inert gas input line connected to the lower end, an inert gas outlet line connected to the upper end thereof and a sample input and reagent inputs located just above the packing, comprising further sample taking means including a sample carrier adapted to be advanced in steps and to receive a series of sample receptacles and a wash liquid receptacle, said sample carrier being movable between a first position, in which one of the sample receptacles is placed in a withdrawal position during the first time period of the measuring cycle, and a second position, in which the wash liquid receptacle is placed in the withdrawal position during the third time period of the measuring cycle, and also including a withdrawal tube adapted to be introduced temporarily into the respective receptacle placed in the withdrawal position, said apparatus also comprising a withdrawal tube connected to the sample input, conduits to connect each of the reagent inputs to a respective reservoir and controlled supply means each governing the sample input and the conduits, respectively, and finally comprising control means designed to control the sample taking means and said supply means in accordance with the method steps during the time periods of each measuring cycle.

Thus, the liquid flow and the inert gas flow through the packed reaction vessel in countercurrent fashion and further 10 mixture of sample and reagent liquids and complete removal of the gaseous measuring sample from the reaction mixture in a particularly efficient manner immediately after formation. No separate stripping and washing devices are required. Connecting the sample input to the withdrawal tube and the reagent inputs to conduits leading from respective reservoirs together with providing controlled supply means governing each enables the supply of even small amounts of liquids and the reactions to be conducted in such a way that mutual contamination of liquid samples or of gaseous measuring samples cannot occur. This advantage is assisted by providing a wash liquid receptacle on the sample carrier in the withdrawal positions of which washing liquid is taken up by the withdrawal tube and delivered to the reactor.

In accordance with the invention the reaction vessel comprises a funnel-shaped discharge section and a packing formed by an insert body having a helical face directed towards the discharge section and having a baffle plate extending upwardly from said helical face to the level of the sample and reagent inputs. In a more simple design the packing is formed by Raschig rings filling the reaction vessel to the level of the sample and reagent inputs. By means of the packing, the liquids supplied to the reaction vessel will become distributed over a large surface area which particularly intensifies the displacement of gases from the liquid reaction mixture by the countercurrent flow of inert gas.

In the apparatus according to the invention the sample carrier is a turntable stepwisely rotatable about its axis on a base plate movable between stops defining the first and the second position of the sample carrier, the wash liquid receptacle being placed on the base plate. The turntable may have a serrated rim and the base plate may be eccentrically pivotably supported on a fixed instrument plate, the base plate having a first ratchet and instrument plate having a second ratchet, both said ratchets being arranged for alternating engagement with said serrated rim so that said turntable will be automatically advanced one step on conclusion of the first time period of the measuring cycle. By combining such a turntable, which is suitable for receiving a great number of sample receptacles, with a pivotable base plate rotating and pivoting movements are favourably combined to bring either the sample receptacle or the wash liquid receptacle into a position for withdrawal of the respective liquid. By means of the interaction of an external serration with appropriately positioned ratchets the pivoting movement of the base plate is combined with the turntable advancement.

According to the invention the base plate may also be arranged for displacement between two stops on a bearing, a return spring acting upon the base plate being secured to one of the stops. Such an arrangement is more favourable with respect to the forces to be provided as compared to pivoting the base plate about an eccentric fulcrum.

In the apparatus according to the invention, the controlled supply means are piston pumps each of which is connected to the sample input or a reagent supply conduit, respectively, intermediate two controlled valves. By combining the piston pumps and controlled valves the piston pumps, which may be connected to the control means in a simple manner, are actuated either to take up the respective liquid or to supply the same to the reaction vessel. Piston pumps have been proven to be particularly useful for conveying small proportionate amounts of liquids. Alternatively, the inert gas source may be connected to a closed reservoir via a service line provided with a first pressure regulator and to the inert gas input line via a second pressure regulator, the input line having two branch conduits including in each an adjustable flow restrictor and being connected to the reaction vessel, the service line and the reagent supply conduit passing through the reservoir closure with the reagent supply conduit extending to the bottom of said reservoir. The supply means may comprise two controlled valves adapted to be actuated in anti-phase relationship one of which is positioned in the service line and the other one in one of the branch conduits. Thus the piston pumps and controlled valves are replaced by pneumatic supply means operated by the inert gas passing through the apparatus and serving as a carrier gas for the gaseous measuring sample. A conduit including an adjustable flow restrictor and a flow meter and interconnecting the branch conduits may be provided to monitor the flow of inert gas during operation of the apparatus.

In and apparatus according to the invention, the wash liquid receptacle is designed as an overflow vessel connected to a wash liquid reservoir by a conduit to which a controlled piston pump is connected intermediate two controlled valves, the piston pump being adapted to be controlled by the control means in accordance with the method steps during the time periods of the measuring cycle. The overflow design of the wash liquid receptacle enables interior and exterior washing of the withdrawal tube before the wash liquid is taken up and delivered to the reaction vessel.

The discharge section of an reaction vessel in the apparatus in accordance with the invention comprises a drain line terminating above a drain liquid container and governed by drain means adapted to be controlled by the control means in accordance with the method steps during the time periods of the measuring cycle. Thus it will be achieved that the reaction vessel will only be emptied after complete reaction of the reaction mixture and after complete removal of the gaseous measuring sample by the inert gas. The drain means comprises a controlled piston pump connected to the drain line intermediate two controlled valves. Thus the drain means may be controlled by the same means controlling the supply means for the different liquids. Alternatively, the drain means may comprise a controlled valve which is possible in cases in which the reaction mixture forms a freely flowing liquid.

In a modification of the apparatus according to the invention a reservoir of a blank liquid free of the element to be determined and similar to the liquid sample is provided and connected to the reaction vessel via a blank input line governed by supply means which are adapted to be controlled by the control means in accordance with the method steps during the time periods of the measuring cycle. Thereby, blank liquid will be supplied to the reaction vessel together with the reagent liquids during the first time period of the measuring cycle. In such a way errors in determining the blank value are avoided which otherwise would occur because of the different liquid volumina introduced into the reaction vessel during the first and during the second time period of the measuring cycle.

To perform reference measurements there is provided in an apparatus according to the invention at least one further reservoir for an addition liquid and one further supply line connected to one further input at the reaction vessel and governed by further supply means adapted to be controlled by the control means in accordance with the method step during the further time periods of the extended measuring cycle. The further reservoir may be placed on the base plate of the sample carrier, the base plate being movable at least into a third position, and a further withdrawal tube connected to the further supply line may be arranged for temporary introduction into the further reservoir in the third base plate position.

To conduct the measurement in a circulation mode the reaction vessel, the inert gas outlet line, the measuring cell and the inert gas input line of the apparatus according to the invention form a closed loop comprising a pressure relief valve downstream from said measuring cell and a circulation pump, a junction with a conduit leading from the inert gas source and governed by a controlled valve formed downstream from the circulation pump, said circulation pump and the valve being adapted to be controlled by the control means in accordance with the method steps during the second and during the further time period of the measuring cycle.

According to the invention, the control means comprises a synchronous motor and a cam shaft driven thereby, the cam shaft including control cams drivingly connected to the supply means and also including additional control cams drivingly connected to the sample taking means, the time of revolution of the cam shaft being equal to the duration of one measuring cycle. Thus, a simple and effective central control of the entire apparatus is achieved. One first additional control cam may be drivingly connected to actuating means acting on the withdrawal tube and a second additional control cam may be drivingly connected to a control lever acting on the base plate against the return spring. In such a way, actuation of the withdrawal tube and movements of the base plate carrying the turntable are most simply effected by the control means. The actuating means for the withdrawal tube comprises a lever system in driving engangement with the first additional control cam movable normally with respect to the plane of the sample carrier. A simple and reliable driving connection is thus established between the control means and the withdrawal tube. Alternatively, the actuating means comprises a pneumatic cylinder including a piston which acts on the withdrawal tube, the pneumatic cylinder being connected to the inert gas input line via a valve controlled by the first additional control cam. In such a way the already present inert gas serving as carrier gas may be utilized for pneumatically actuating the withdrawal tube by the control means.

In an apparatus according to the invention, the cam shaft may be provided with a first further control cam drivingly connected to the piston pump for wash liquid. Thus washing of the apparatus is being controlled centrally, also. To realize pneumatic actuation of the piston pump for wash liquid, the first further control cam may alternatively be in driving connecting to a valve controlling a pneumatic cylinder the piston of which acts on the piston pump and which is connected to the inert gas input line.

A second further control cam may be provided in the apparatus in accordance with the invention, the second further control cam being drivingly connected to the drain means. Thus, draining the reaction vessel will be centrally controlled, too. The second further control cam may form a control plate acting on the piston pump of the drain means and providing a mechanical driving connection of the cam shaft and the drain means. Alternatively, the second further control cam may act upon a control valve governing the control line of a pneumatically controlled drain valve which control line is connected to the inert gas input line. In the case of reaction liquids which will flow freely from the reaction vessel there is thus provided a particularly simple central control of the drain means by employing the available inert gas.

Specific embodiments of the invention are illustrated in the drawings and will be described with reference thereto in detail hereinbelow.

DESCRIPTION OF SPECIFIC EMBODIMENTS

Figure 1:
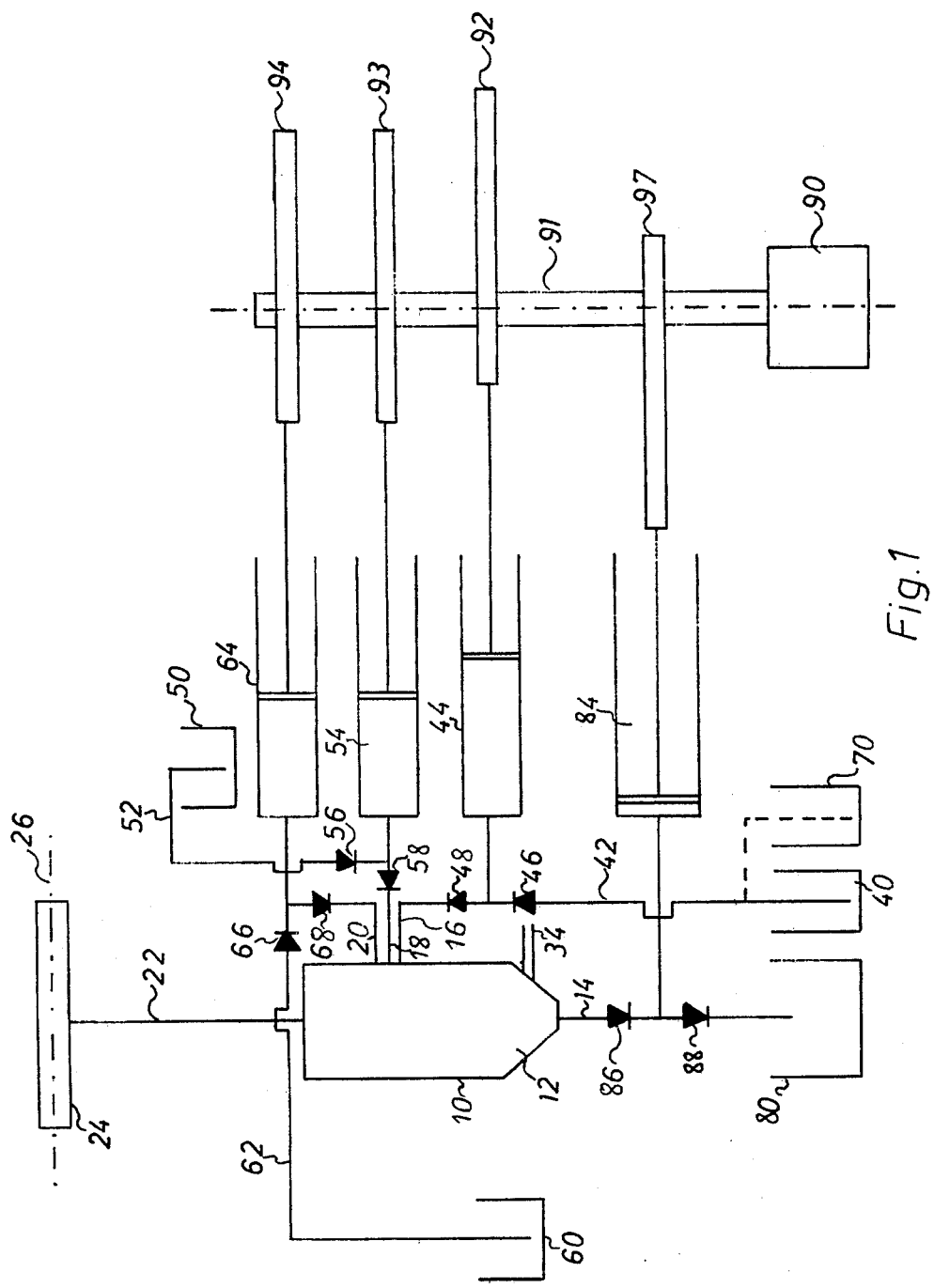
FIG. 1 is a schematic representation of a first embodiment of the apparatus according to the invention.

In the schematic representations of the apparatus for automatically generating and measuring gaseous measuring samples from a series of liquid samples the reaction vessel generally has reference numeral 10. Reaction vessel 10 has a funnel-shaped discharge section 12 including a drain line 14. Three inputs open into reaction vessel 10, namely, a sample input 16 and two reagent inputs 18,20. One connecting conduit extends from the upper end of reaction vessel 10 and another one opens into discharge section 12. The latter one represents inert gas input line 34 and the first one is inert gas outlet line 22 connected to a heatable measuring tube 24 formed, for instance from graphite which is placed in the optical path of rays 26 in a atomic absorption spectrometer.

Figure 9:
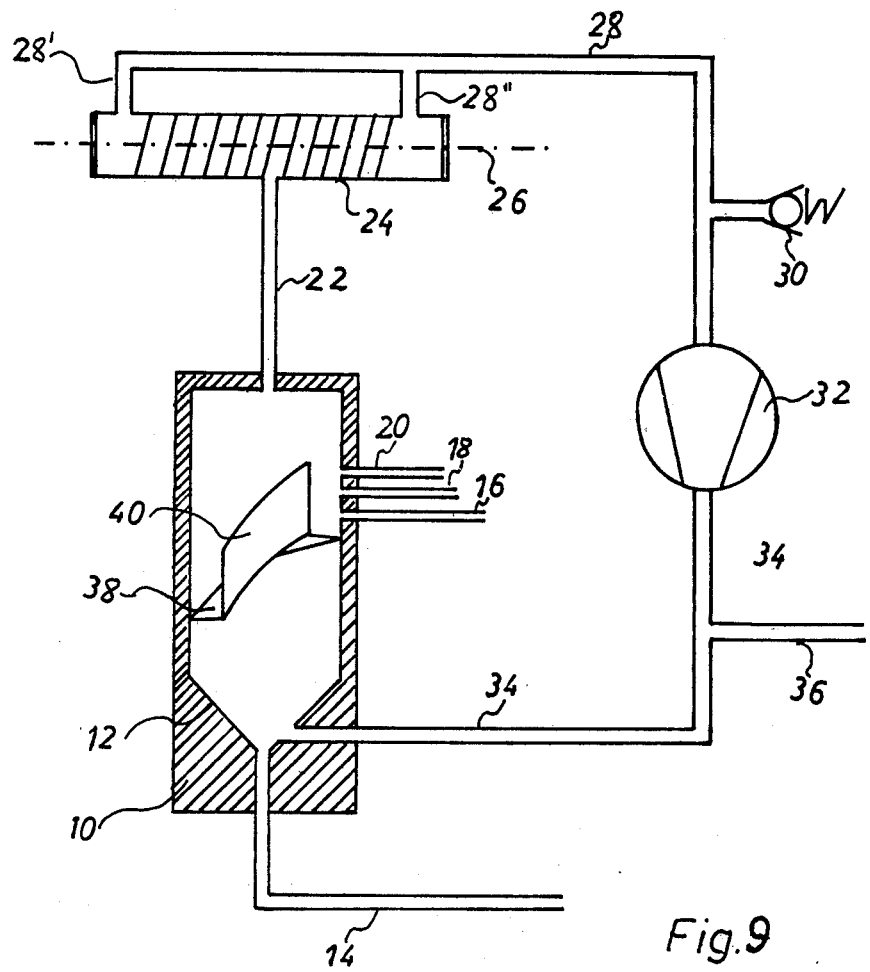
FIG. 9 is a partially sectional schematic representation of a third embodiment of the apparatus according to the invention.

Details of reaction vessel 10 may be recognized from FIG. 9 in which a sectional view thereof is shown diagrammatically. A helical face 38 is seen in the interior of the vessel to extend downwardly towards the funnel-shaped discharge section 12 and to have a baffle plate 40 extending normally and upwardly therefrom. Helical face 38 is made of corrosion resistant material mounted within the interior of reaction vessel 10 in a suitable manner. Baffle plate 40 projects upwardly to the level at which sample input 16 and reagent input 18,20 open into reaction vessel 10.

FIG. 1 further shows a sample receptacle 40 and a withdrawal tube introduced into receptacle 40, withdrawal tube 42 being connected to sample input 16. Sample input 16 is governed by supply means comprising a controlled piston pump 44 and two series connected check valves 46,48 intermediate which the piston pump is connected to the sample input 16. Furthermore, a wash liquid receptacle 70 is shown in FIG. 1, dashed lines indicating the withdrawal tube 42 can be introduced into the same. Therefore, wash liquid, too, will be supplied to reaction vessel 10 via sample input 16 by means of withdrawal tube 42, piston pump 44 and check valves 46,48.

A reservoir 50 containing a first liquid reagent is connected to reagent input 18 via a conduit 52 governed by a piston pump 54 and two series connected check valves 56,58 intermediate which piston pump 54 is connected to conduit 52. Another reservoir 60 containing a second liquid reagent is connected to reagent input 20 via a conduit 62 governed by a piston pump 64 and two series connected check valves 66,68 intermediate which piston pump 64 is connected to conduit 20. Drain line 14 of reaction vessel 10 ends in a drain liquid container 80 and is governed by a piston pump 84 and two series connected check valves 86,88 intermediate which piston pump 84 is connected to drain line 14.

The control means of the apparatus shown diagrammatically in FIG. 1 comprises a synchronous motor 90 driving a cam shaft 91. Cam shaft 91 carries a control cam 92 forming a control plate for driving piston pump 44, a control cam 93 forming a control plate for driving piston pump 54, and a control cam 94 forming a control plate for driving piston pump 64. Furthermore, cam shaft 91 carries a further control cam 97 forming a control plate for driving piston pump 84.

Figure 3:
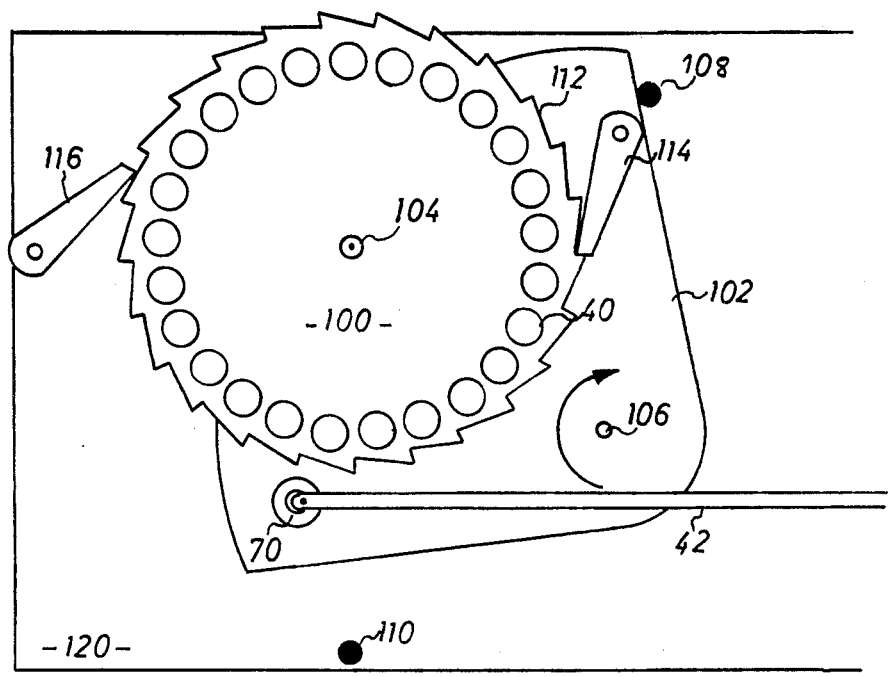
FIGS. 2 and 3 are plan views of the sample taking means in the apparatus as in FIG. 1 with a sample receptacle and the wash liquid receptacle, respectively, in withdrawal position.
Figure 2:
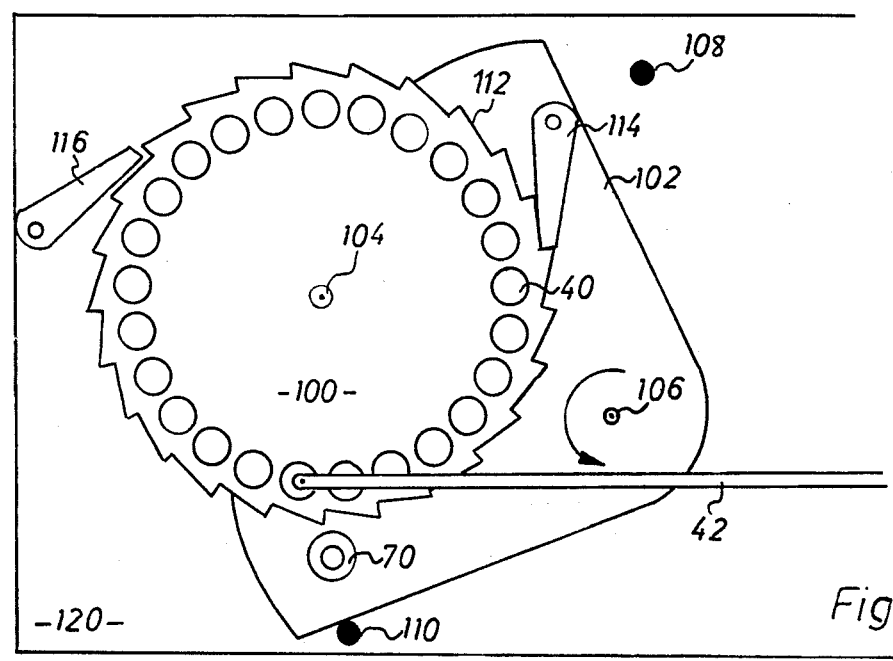

FIG. 2 shows a plan view of the sample taking means not shown in FIG. 1. A turntable 100 carrying an annularly arranged series of sample receptacles 40 is mounted on a base plate 102 for rotation about its central axis 104. Base plate 102 is mounted on a fixed instrument plate 120 for pivoting about an eccentric fulcrum 106 between two stops 108,110 on fixed instrument plate 120. Turntable 100 has an external serration into which ratchets 114,116 engage. Ratchet 114 is secured to the base plate 102 and ratchet 116 is secured to fixed instrument plate 120. In the position as shown in FIG. 2 base plate 102 abuts stop 110 and one sample receptacle 40 is positioned below withdrawal tube 42, while in the position as shown in FIG. 3 base plate 103 abuts stop 108 and the wash liquid receptacle 70 is positioned below withdrawal tube 42. It will also be seen from FIGS. 2 and 3, that because of the engagement of ratchet 116 with the external serration 112 on the turntable 100 the turntable will be advanced by one step each time the base plate 102 becomes pivoted towards stop 110.

Figure 4:
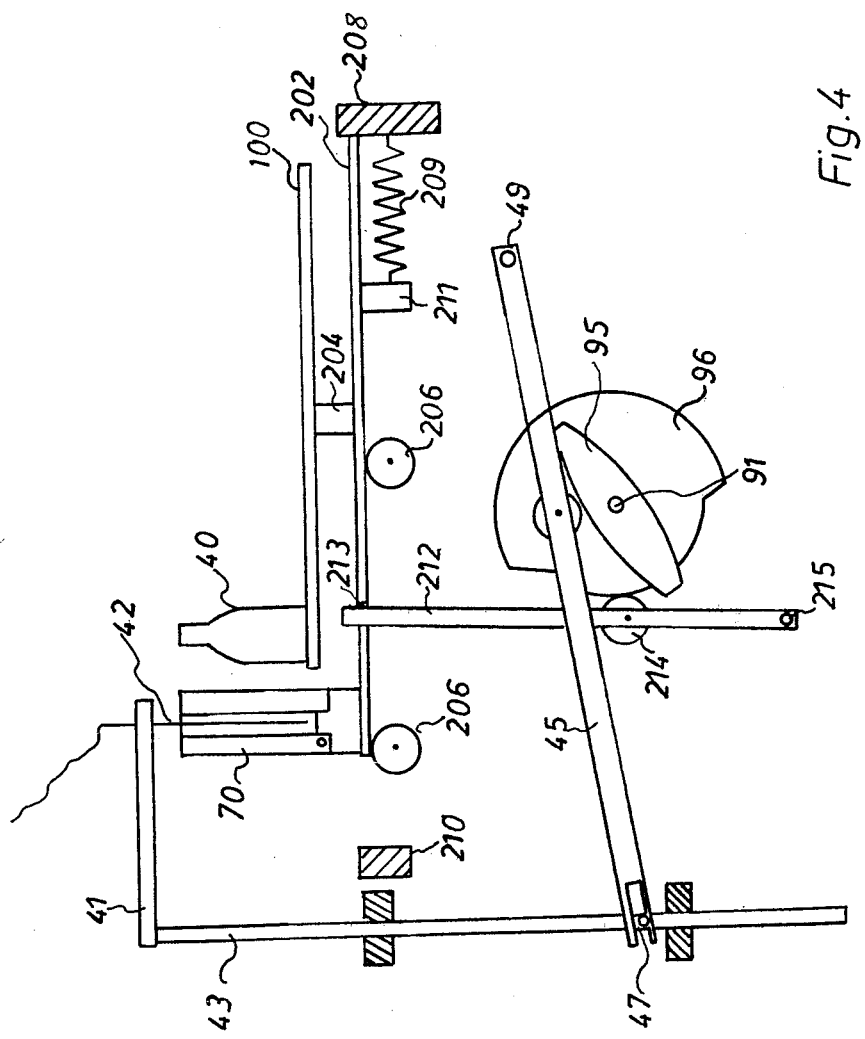
FIG. 4 is a partially schematic cross sectional view of a modified form of sample taking means.

In the modified sample taking means as shown in FIG. 4 the turntable 100 carries a sample receptacle 40 represented in enlarged size. Turntable 100 is stepwisely advanced about the axis of a connective member 204 connecting the turntable 100 to a base plate 202. Base plate 202 is arranged to be movable longitudinally on bearings 206 between stops 208,210 against the force of a return spring 209 mounted at stop 208 and acting on a lug 211 at the underside of base plate 202. As in the embodiment shown in FIGS. 2 and 3, the wash liquid receptacle 70 is located on base plate 202. One end of a lever 212 extends into a cap 213 in base plate 202, the other end being pivotably supported as at 215. Intermediate its ends lever 212 carries a follower 214 drivingly engaged to cam shaft 91.

Furthermore, there is represented in FIG. 4 a lever gear acting on withdrawal tube 42 for reversibly introducing the same into a sample receptacle 40 or wash liquid receptacle 70 depending on the position of base plate 202. The lever gear comprises an L-shaped lever the short leg 41 of which is secured to the withdrawal tube 42 while the long leg 43 thereof is guided between guidance means for reciprocating rectilinear movement. The long leg 43 is pivoted to one end 47 of a pivoting lever 45, the other end 49 of which is pivotably supported. Pivoting lever 45 carries a follower intermediate its ends which is in driving connection with control cam 95 on cam shaft 91.

The lever gear 41,43,45 as shown in FIG. 4 may also be employed in connection with the arrangement as shown in FIGS. 2 and 3.

The cam shaft 91 is provided with a first additional control cam 95 acting on the follower carried by pivoting lever 45 to effect the vertical movement of withdrawal tube 42. Cam shaft 91 has a second additional control cam 96 acting on lever 212 via cam follower 214 to effect the longitudinal displacement of base plate 202 against the force of return spring 219.

Further details of the sample taking means are described in U.S. Pat. No. 4,111,051 issued Sept. 5, 1978 of common assignee herewith.

Figure 5:
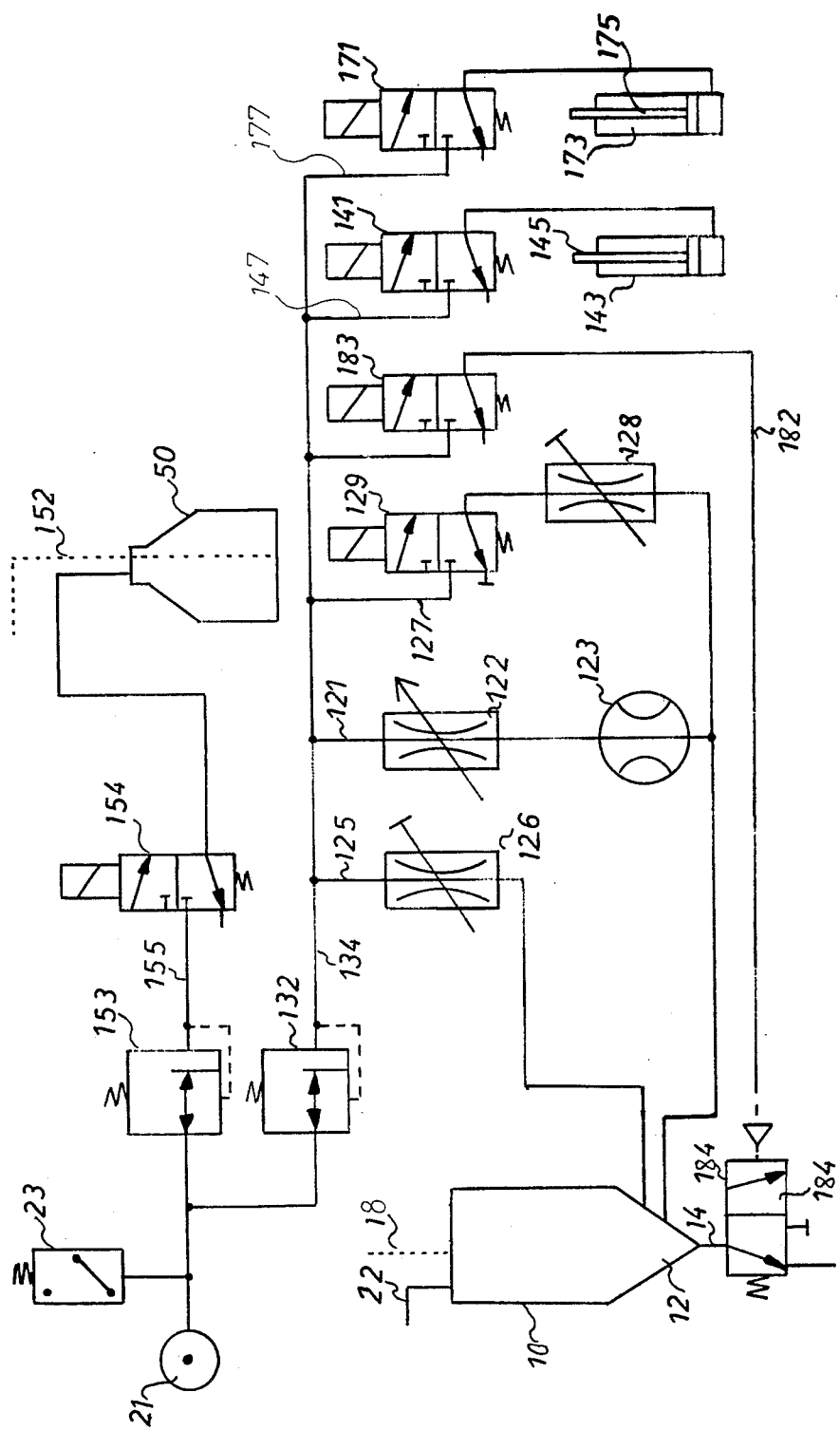
FIG. 5 is a schematic representation of a detail of a second embodiment of the apparatus according to the invention.

FIG. 5 shows diagrammatically part of a second embodiment of the apparatus as shown in FIG. 1 in which pneumatic supply means for the reagent supply from reservoir 50 are provided. Therefor, reagent input 18 is connected to a supply conduit 152 extending through the closure of closed reservoir 50 to the bottom thereof. An inert gas source 21 is connected via a pressure switch 23 to the inputs of a first pressure regulator 153 and a second pressure regulator 132 connected in parallel thereto. The output of first pressure regulator 153 is connected to a service line 155 leading to reservoir 50 and extending just through the closure thereof. Inert gas pressure in the service line 155 is regulated to a value of approximately 0.15 bar by means of first pressure regulator 153. Service line 155 is governed by a 2/2-way valve formed as a solenoid valve controlled via cam shaft 91 and a suitable control cam thereon. The output of the second pressure regulator 132 is connected to inert gas input line 134 branched into two branch conduits 125,127 which are joined to the funnel-shaped discharge section 12 of reaction vessel 10. Both the branch conduits 125,127 are provided each with respective adjustable flow restrictors 126,128. Branch conduit 127 is governed by a 2/2-way valve formed as a solenoid valve controlled via cam shaft 91 and a suitable control cam thereon. Branch conduits 125,127 are interconnected by a conduit 121 including an adjustable flow restrictor 122 and a flow meter 123. By means of the second pressure regulator 132 the pressure in the inert gas input line 134 is regulated to a value of approximately 1.4 bar. Practically, the supply means is formed by the two 2/2-way valves 154,129 operated in an antiphase relationship so that valve 154 will only be opened if valve 129 is closed and vice versa.

Thus inert gas pressure will be applied to reservoir 50 only when inert gas is fed to reaction vessel 10 through relatively strongly restricted branch conduit 125 so that the inert gas pressure prevailing within reaction vessel 10 will not oppose the supply of reagent liquid thereto through supply conduit 152.

Correspondingly designed supply means are provided for the supply of the second liquid reagent from reservoir 60.

FIG. 5 shows further details of a pneumatic control for other components of the apparatus for generating and measuring gaseous measuring samples from a series of liquid samples. The pneumatic control means as shown in connection with the embodiment of the apparatus as in FIG. 5 may also be utilized in the embodiment of the apparatus as in FIG. 1 and FIG. 2 instead of part or all of the mechanical control means shown therein.

In the embodiment as shown in FIG. 5 the drain line 14 is governed by a controlled 3/2-way valve replacing the piston pump 84 and the check valves 86,88 in the embodiment of FIG. 1. The 3/2-way valve 84 is controlled pneumatically through control line 182 which is governed by a 2/2-way valve 183 and which is connected to the inert gas input line 134 in parallel to branch conduits 125,127. The 2/2-way valve 183 is a solenoid valve controlled via cam shaft 91 and a suitable control cam thereon. Since the drain means as shown herein are devoid of a pump, said drain means can only be employed with liquids which will freely flow from reaction vessel 10 on opening valve 184.

FIG. 5 also shows pneumatic control means for the piston pump 44 of the sample taking means. A 2/2-way valve 141 formed as a solenoid valve is controlled via cam shaft 91 and a suitable control cam thereon. A pneumatic cylinder 143 has an adjusting piston 145 drivingly connected to piston pump 44. Valve 141 governs a conduit 147 connecting pneumatic cylinder 143 to the inert gas input line 134 in parallel to branch conduits 125,127.

Furthermore, pneumatic control means for the supply of wash liquid are shown in FIG. 5 and will be further explained in connection with FIG. 6. The control means comprises a 2/2-way valve 171 formed as a solenoid valve controlled via cam shaft 91 and a suitable control cam thereon, a pneumatic cylinder 173 having an adjusting piston 175 drivingly connected to a wash liquid piston pump (not shown) and a conduit 177 connecting pneumatic cylinder 173 to the input gas input line 134 in parallel to branch conduits 125,127 and governed by 2/2-way valve 171.

Figure 6:
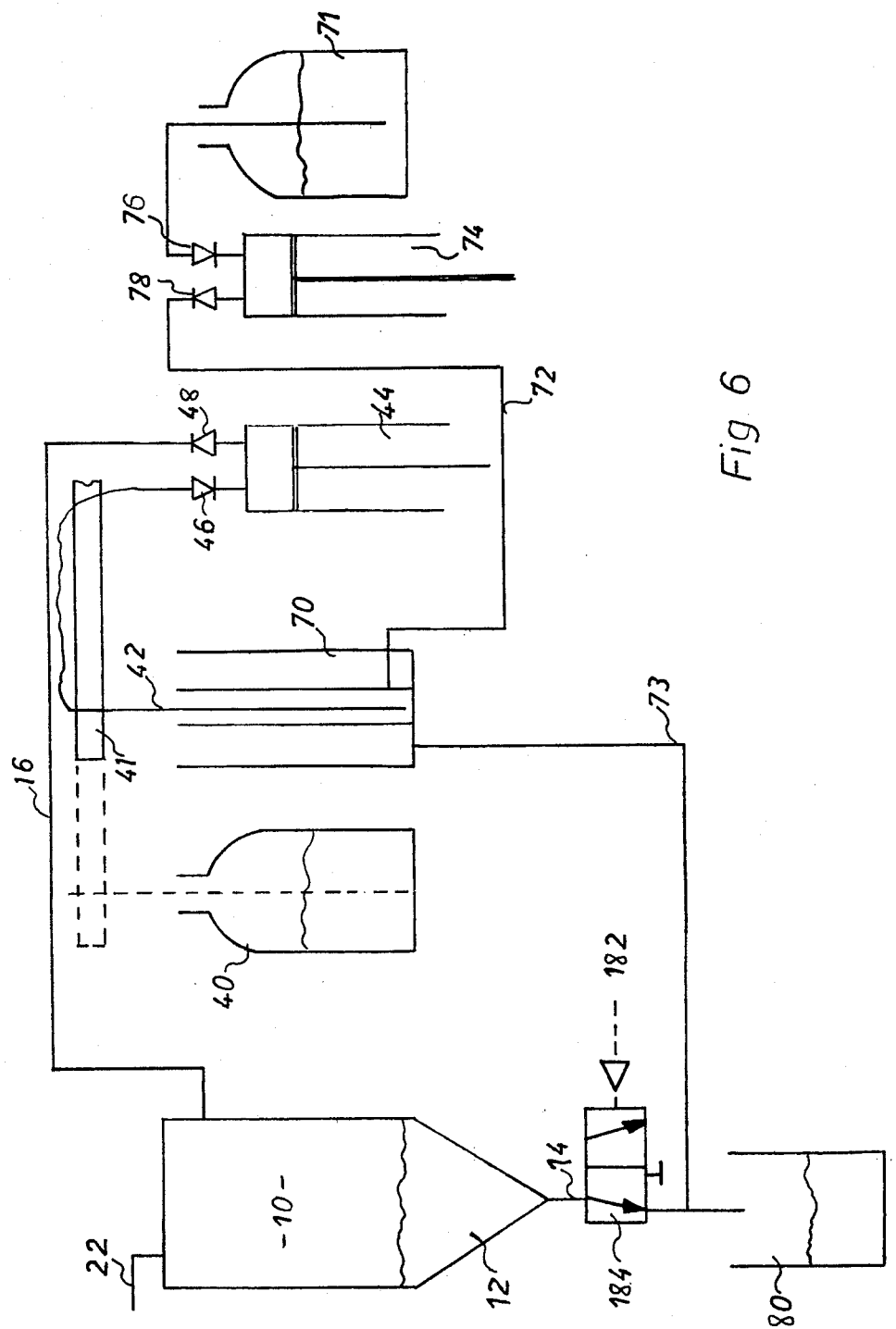
FIG. 6 is a schematic representation of another detail of the second embodiment of the apparatus according to the invention.

FIG. 6 shows another detail of the embodiment of the apparatus as in FIG. 5. Reaction vessel 10 is shown with inert gas outlet line 22 while branch conduits 125,127 forming the inert gas input are omitted for simplicity. Drain line 14 extending from the funnel-shaped discharge section 12 ends above the drain liquid container 80 and is governed by the 3/2-way valve 184 controlled pneumatically via control line 182. As shown in the embodiment according to FIG. 1 the withdrawal tube movable by a lever 41 into either one sample receptacle 40 or the wash liquid receptacle 70 is connected to the sample input 16 governed by piston pump 44 and the series connected check valves 46,48. Furthermore, in the embodiment shown in FIG. 6 a wash liquid reservoir 71 is connected to wash liquid receptacle 70 through a supply conduit 72. Wash liquid receptacle 70 is designed as an overflow vessel with supply conduit 72 opening into the interior overflow compartment of the vessel and a discharge line 73 leading from the bottom of the exterior compartment of the vessel to drain line 14 downstream of drain valve 184. Supply conduit 72 is governed by supply means comprising a piston pump 74 and two series connected check valves 76,78 intermediate which piston pump 74 is connected to supply conduit 72. The piston pumps 44,74 are in driving engagement to adjusting pistons 145 and 175, respectively, of pneumatic cylinders 143 and 173, respectively, as shown in FIG. 5. Alternatively, either one or both of piston pumps 44,74 may be in mechanical driving connecting to cam shaft 91 in the way as shown for the embodiment according to FIG. 1.

Figure 7:
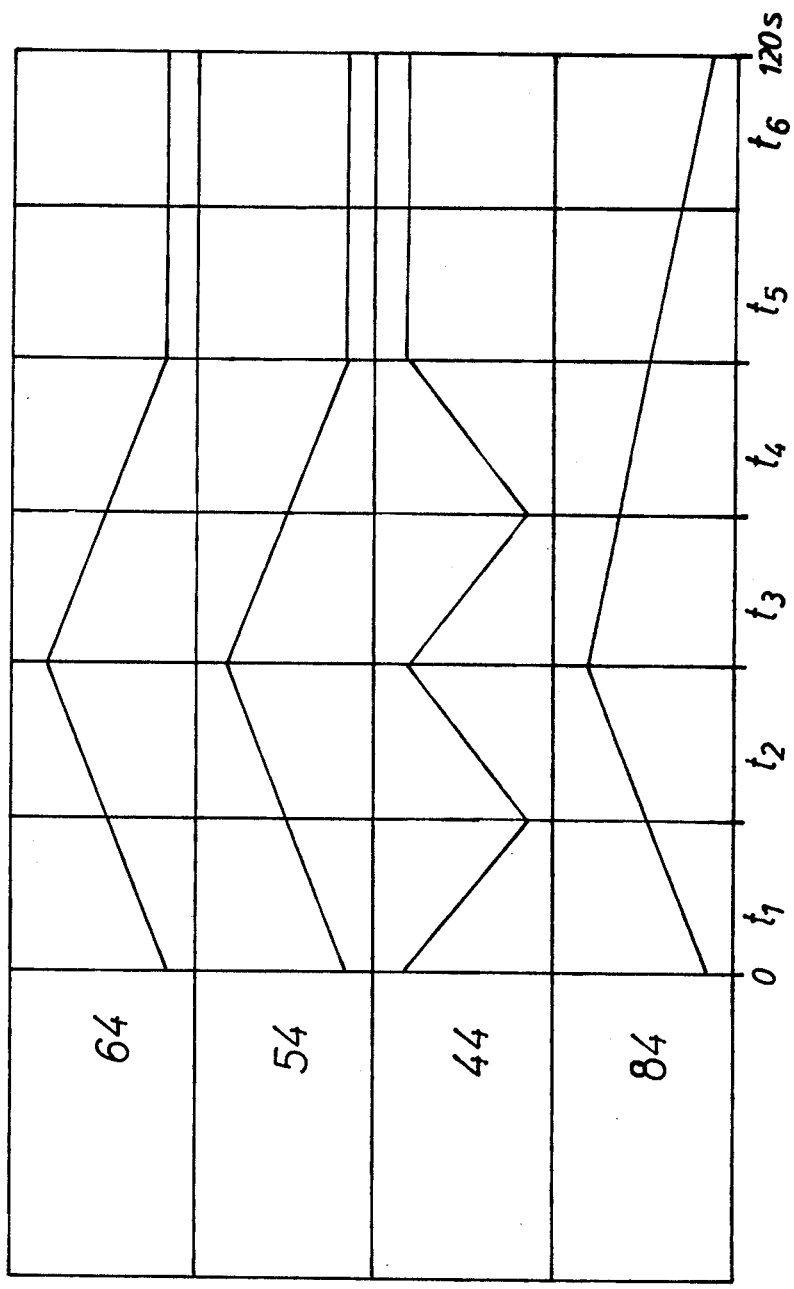
FIG. 7 is a diagram of some of the steps included in the method according to the invention.

The time sequence of the operation of the supply means as shown in the embodiment of the apparatus in FIG. 1 is illustrated diagrammatically in FIG. 7 for one measuring cycle of 120 seconds. The displacements of the pistons in piston pumps 44,54,64, and 84 are represented in an analogous way in which an ascending line denotes liquid discharge and a descending line denotes liquid uptake by the respective pump. At the beginning of each measuring cycle liquid reagents will be supplied to reaction vessel 10 by piston pumps 54,64 for the determination of the blank value. Durng the time period $t_1$ of the measuring cycle base plate 102 of the sample taking means abuts stop 110 so that one sample receptacle 40 is positioned below withdrawal tube 42 which is introduced into the same. Piston pump 44 is operated to take up liquid sample. Thereby, check valve 48 prevents the intake of inert gas from reaction vessel 10 and, correspondingly, check valves 56,66 prevent that the liquid reagents taken up by piston pumps 54,64 are returned into the respective reservoirs 50,60. During the following time period $t_2$ the supply of liquid reagents by piston pumps 54,64 is continued, however, in parallel therewith liquid sample, too, is supplied to reaction vessel 10 through sample input 16 by piston pump 44, check valve 46 preventing return to withdrawal tube 42. During both time periods, $t_1, t_2$ the reaction mixture from the previous measuring cycle as taken up from the reaction vessel by piston pump 84 via drain line 14 is discharged into the drain liquid container 80, check valve 86 preventing return of the reaction mixture through drain line 14 to reaction vessel 10. After conclusion of the second time period $t_2$ and reaction is completed; piston pumps 54,64, then, are reversed to take up a new charge of liquid reagents from reservoirs 50,60 during the time periods $t_3,t_4$. During the third time period $t_3$ base plate 102 of the sample taking means abuts stop 108 and withdrawal tube is immersed into wash liquid receptacle 70; during this time period, therefore, wash liquid is taken up by piston pump 44. During the fourth time period $t_4$ the wash liqid is substantially supplied to reaction vessel 10. During the subsequent time periods $t_5,t_6$ piston pumps 44,54,64 remain in the positions assumed at the end of the fourth time period $t_4$ and thus are prepared for the next following measuring cycle. During the time periods $t_3$ to $t_6$ the reaction vessel 10 is gradually emptied by means of piston pump 84 which takes up the entire reaction mixture. The wash liquid supplied to reaction vessel 10 during the fourth time period $t_4$ will finally be transferred to piston pump 84.

A corresponding sequence will be obtained with the embodiment of the apparatus as in FIG. 5 in which each of piston pumps 54,64 is replaced by controlled 2/2-way valves 154 which is opened during the time periods $t_1,t_2$, while the valve 129 positioned in branch conduit 127 of inert gas input line 134 is closed. Instead of the drain means comprising piston pump 84 and check valves 86,88 in this modification the 3/2-way valve 184 is used which is closed during time periods $t_1$ and $t_2$ and which is open during the remaining time periods of the measuring cycle.

In both the embodiments of the apparatus according to either FIG. 1 or FIG. 5, respectively, the wash means as illustrated in FIG. 6 in detail may be employed. While the operational sequence of steps of piston pump 44 will remain unchanged thereby, piston pump 74 connected to supply conduit 72 leading from wash liquid reservoir 71 to wash liquid receptacle 70 will be operated in such a way that either during time period $t_1$ or time period $t_2$ or during both time periods $t_1,t_2$ wash liquid is taken up from wash liquid reservoir 71 and supplied to wash liquid receptacle 70 either during time period $t_3$ or during time periods $t_3,t_4$.

To illustrate the operative sequence in detail with respect to the apparatus as shown in FIG. 1, the analytical determination of for instance arsenic is described hereinbelow.

Before the start of a series of measurements sample receptacles 40 containing respective liquid samples are inserted into turntable 100 which is in the position of FIG. 2. Reservoir 50 contains a 5 percent aqueous solution of sodium borohydride and reservoir 60 10 percent aqueous hydrochloric acid. Wash liquid receptacle 70 is filled with pure water. Before the start of each measuring cycle reaction vessel 10 and measuring tube 24 are flushed through inert gas input line 34 with inert gas which flows initially at a higher rate to more rapidly displace the air from the apparatus. Furthermore, piston pumps 54,56 are actuated in such a way as to be filled with the respective liquid reagents. As shown in FIG. 2, withdrawal tube 42 is positioned right above the sample receptacle 40 placed in withdrawal position. Piston pump 44 is actuated so as to assume one extreme position (not shown in FIG. 1) from which the pump will be further actuated to take up liquid sample. Withdrawal tube 42, sample input 16, supply conduits 52,62 and reagent inputs 18,20 are completely filled with liquid to ensure that at no instance during the following procedure air or gas bubbles are supplied by anyone of piston pumps 44,54,64. Measuring tube 24 is heated to a temperature of approximately 900 degrees centigrade and the atomic absorption spectrometer is adjusted to the wavelength characteristic for the measurement of arsenic.

To start the first measuring cycle synchronous motor 90 is energized to rotate cam shaft 91. Initially, during time period $t_1$, the levers 41,43,45 will be actuated by means of the first additional control cam 95 to introduce withdrawal tube 42 into sample receptacle 40. Then piston pump 44 is operated by means of control cam 92 to take up liquid sample. In parallel therewith, piston pumps 54,64 are operated by means of control cams 93,94 to supply the liquid reagents to reaction vessel 10 during the first time period $t_1$. The liquid reagents are distributed over helical face 38 by means of baffle plate 40 and run along face 38 towards the funnel-shaped discharge section 12 of reaction vessel 10. During that time, inert gas entering through inert gas input line 34 is led in countercurrent fashion against the flow of the reaction liquid and entrains the gas formed therein. Through inert gas outlet line 22 the gas stream enters measuring tube 24 and leaves the same through its open ends. During this time the atomic absorption is measured to determine the blank value which will have to be subtracted from the measured value later. At the end of time period $t_1$ piston pump 44 is filled with liquid sample; by means of levers 41,43,45 as controlled by first additional control cam 95 withdrawal tube 42 is lifted from the sample receptacle 40.

At the start of the second time period $t_2$ of the measuring cycle base plate 102 of the sample taking means is pivoted about fulcrum 106 so as to abut stop 108, wash liquid receptacle 70 now being positioned below withdrawal tube 42. Pivoting is effected by means of a second additional control cam on cam shaft 91 drivingly connected to a suitable pivoting mechanism. When base plate 102 arrives at the new position the first additional control cam 95 will again effect actuation of levers 41,43,45 to lower withdrawal tube 42 and introduce the same into wash liquid receptacle 70. During the second time period $t_2$ the liquid sample taken up by piston pump 44 will be discharged into reaction vessel 10 through sample input 16 parallel and in common with the liquid reagents. Also, during the second time period $t_2$ the inert gas stream with the entrained gaseous measuring sample formed in the reaction mixture is fed to measuring tube 24. During this time any arsenic present in the sample will form arsine in the reaction vessel 10 which is removed therefrom and introduced into the measuring tube 24 heated to 900 degrees centigrade so that the arsine is decomposed to form arsenic in the atomic state. During the second time period $t_2$ the atomic absorption of arsenic is being measured. At the end of time period $t_2$ piston pumps 44,54,64 have supplied all their contents to reaction vessel 10.

Just before conclusion of time period $t_2$ or immediately at the start of the third time period $t_3$ withdrawal tube 42 is introduced into wash liquid receptacle 70. A further control cam 97 on cam shaft 91 which is in driving connection with piston pump 84 of the drain means reverses said pump the volume of which is selected such that the entire volume of liquid as supplied by piston pumps 44,54,64 can be taken up. Piston pump 84 is operated also through all remaining time periods $t_4$ to $t_6$ of the measuring cycle thus gradually removing all the liquid contained in reaction vessel 10. In parallel therewith and during the third time period $t_3$ piston pump 44 is actuated via control cam 92 to take up wash liquid filling the same at the end of this time period. Simultaneously, piston pumps 54,64 are actuated via control cams 93,94 to take up liquid reagent from reservoirs 50 and 60, respectively, and the pumps will be filled therewith on conclusion of the fourth time period $t_4$.

During the pivoting movement of base plate 102 towards abutment to stop 108 the ratchet 114 engaged with the external serration 112 of turntable 100 will advance the same by one step so that after return of base plate 102 into abutment to stop 110 the sample receptacle 40 following next in the series is located in withdrawal position.

After piston pump 44 has been filled with wash liquid during the third time period $t_3$ the withdrawal tube 42 will be lifted from wash liquid receptacle 70 by means of levers 41,43,45 due to the further revolution of the first additional control cam 95. During the following time periods $t_4$ to $t_6$ withdrawal tube 42 will remain in the lifted position.

During the fourth time period $t_4$ piston pump 44 is operated by means of control cam 92 on cam shaft 91 to supply wash liquid to reaction vessel 10. Starting from baffle plate 40 the wash liquid is distributed over the helical face 38 washing away any liquid material that might have remained thereon. Subsequently to the reaction liquid the wash liquid enters the funnel-shaped discharge section 12 and is removed from reaction vessel 10 through the action of piston pump 84. At the end of the last time period $t_6$, therefore, the reaction vessel 10 is washed and available for investigating the next liquid sample in the series. By means of control cam 92 the piston pump 44 is adjusted to one extreme operative position for taking up further liquid; it will stay in this position through the remaining time periods $t_5$ and $t_6$.

After conclusion of the second time period $t_2$ the actual analytical measurement is concluded, too. However, inert gas is kept being supplied to reaction vessel 10 and measuring tube 24 through inert gas input line 24 to prevent air from entering the apparatus. As desired, heating of measuring tube 24 may be continued or interrupted through time periods $t_3$ to $t_6$ of the measuring cycle.

On conclusion of the fourth time period $t_4$ piston pumps 44,54,64 are in stand-by state for the analysis of the next following liquid sample. During time periods $t_5$ and $t_6$ the remaining reaction liquid and the wash liquid are removed from reaction vessel 10 and taken up by piston pump 84. At the end of the sixth period $t_6$ the measuring cycle is concluded.

Piston pump 84 is controlled in its operation by means of further control cam 97 on cam shaft 91 in such a way that the reaction liquid taken up will be discharged into drain liquid container 80 during the first two time periods $t_1$, $t_2$ of the subsequent measuring cycle.

Figure 8:
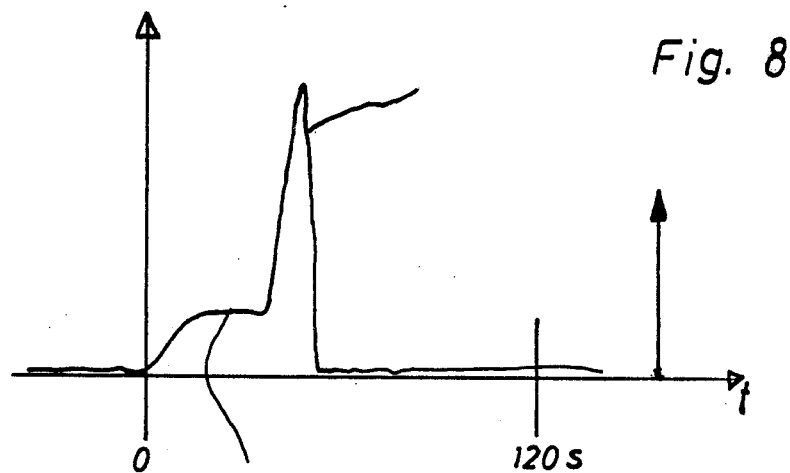
FIG. 8 is a record of the analytical result obtained by carrying out the method according to the invention.

The analytical measuring results obtained during each measuring cycle are continuously recorded. The record trace for one measuring cycle is reproduced in FIG. 8 which shows the extinction in measuring tube 24 as a function of time. The signal recorded during the first time period $t_1$ is clearly recognized; in the case under investigation the liquid reagents contained arsenic the atomic absorption of which is measured and yields a stepped-up base line from which the blank value is calculated. During the time period $t_2$ the extinction rapidly increases to the measuring value from which the arsenic contained in the liquid sample is determined in conventional manner.

The method is performed in corresponding fashion with apparatus having the base plate 202 arranged for longitudinal displacement as in FIG. 4, having pneumatic supply means as in FIG. 5 for the liquid reagents, or having a wash liquid receptacle designed as an overflow vessel in combination with piston pump 74 and drain means comprising controlled 3/2-way valve 184. No further explanation thereof is required here, therefore.

For precise determination of the blank value it is important to note that in the method as carried out using the apparatus described hereinbefore the amount of liquid supplied to reaction vessel 10 during the first time period $t_1$ is different from that supplied during the second time period $t_2$. While the inert gas pressure prevailing in reaction vessel 10 will remain constant during this time, the proportion of the gaseous measuring sample remaining in the reaction liquid will thus be different during the two time periods. To avoid any errors resulting therefrom it is expedient to supply a blank liquid to reaction vessel 10 in addition to the liquid reagents during the first time period $t_1$. The blank liquid should be selected such that the solubility of the gaseous measuring sample therein would be comparable to the solubility in the liquid sample. The blank liquid is introduced into reaction vessel 10 through a further input corresponding to reagent supply inputs 18,20 and the further input is governed by anyone of the aforementioned supply means adapted to be controlled correspondingly by cam shaft 91. Alternatively, the supply means may comprise a withdrawal tube arranged for reciprocating movement as withdrawal tube 42 but with respect to a blank liquid reservoir placed on turntable 100 or base plate 102 or 202, respectively.

In the case of liquid samples to be investigated in which no linear or known relationship of the extinction as measured by the atomic absorption spectrometer to the concentration or, respectively, to the amount of the element to be determined in the liquid sample exists, reference measurements are taken within each measuring cycle. Therefor, further supply inputs for addition liquids containing known amounts of the element to be determined are provided at reaction vessel 10 and the addition liquids are supplied thereto after each respective sample has been measured. The further supply inputs are connected to respective reservoirs through supply conduits governed by anyone of the aforementioned supply means. In an alternative arrangement, the addition liquid reservoirs are placed on base plate 102 or 202, respectively, which is movable into more than two positions, the withdrawal tube 42 being introduced successively into the sample receptacle 40 and the addition liquid reservoir. Suitable means for moving the base plate into the respective positions are described in German Offenlegungsschrift No. 2507260. A wash step will be interposed between each uptake of liquid.

In the case of reference measurements each measuring cycle will be extended by further time periods $T_1, T_2$ etc. in correspondence with the respective number of addition liquids to be measured. The further time periods follow the second time period $t_2$. The drain means is, then, adapted to the respective addition liquid supply means in that the reaction vessel 10 is emptied after completion of each single measurement, i.e. a number of times within each measuring cycle after measuring the liquid sample and after measuring each of the addition liquids, or after completion of each extended measuring cycle, respectively.

The method and the apparatus for carrying out the same as described hereinbefore can be applied to all liquid samples yielding a gaseous measuring sample on reaction with appropriate reagents in reaction vessel 10. Heating of measuring tube 24 and wave length adjustments at the atomic absorption spectrometer are varied accordingly. Under corresponding conditions the same method may be utilized for the determination of antimony, lead, selenium or of all other elements forming volatile hydrides which may be thermally decomposed to form the respective atoms the atomic absorption of which can be measured.

A further variation of the apparatus adapted for mercury determination is shown diagrammatically in FIG. 9. The modified apparatus differs from that described hereinbefore in that the heatable measuring tube 24 is closed by optically transparent windows and has outlets 28' and 28" near both its ends communicating with a common return line 28 which is connected to inert gas input line 34. The inert gas input line 34 is connected to inert gas source 21 by a branch 36 governed by a controlled valve. Return line 28 includes a vent with a check valve 30 and a circulation pump 32, the vent being positioned upstream of pump 32. To carry out the method, reservoir 50 is filled with a 1 percent aqueous tin-II-chloride solution and reservoir 60 with dilute sulphuric acid. On mixing the liquid reagents with a liquid sample containing containing mercury elemental mercury is formed which is stripped from the reaction mixture by the inert gas stream and introduced into measuring tube 24 which is heated to approximately 200 degrees centigrade inert gas outlet line 22. Measuring tube 24 again is positioned in the optical path of rays 26 of the atomic absorption spectrometer which is adjusted to a wavelength suitable for measuring the atomic absorption of mercury. In the present modification the method as described hereinbefore is conducted in such a way that after conclusion of the first time period $t_1$ during which the blank value has been detected and before the start of the second time period $t_2$ during which the liquid sample is supplied to reaction vessel 10 a further time period $T_u$ is interposed. During the further time period $T_u$ the value governing branch 36 is closed and circulation pump 32 is energized. Thus the mercury containing inert gas enclosed in inert gas input line 34, reaction vessel 10, inert gas outlet line 22, measuring tube 24, outlets 28',28" and return line 28 is circulated, the atomic absorption of mercury being measured continuously. After obtaining a constant extinction signal from which the mercury contents in the liquid sample is determined in conventional known manner circulation pump 32 is de-energized, the valve governing branch 36 is reopened and the method steps are then conducted as intended for time periods $t_3$ through $t_6$. The vent including check valve 30 serves to let off any excessive pressure that might develop during circulation.

I claim:

1. An automatic system for generating gaseous samples from liquid samples and reagents and for transferring gaseous samples for measurements in an atomic absorption spectrometer, said system comprising:

means defining a reaction chamber having a first outlet in communication with an absorption spectrometer measuring cuvette and first, second, and third inlets for injecting liquid samples and first and second liquid reagents respectively into said chamber;

said reactor including a helical spillway adjacent its inner surface, said spillway having a vertical side wall for receiving injected fluids and directing said fluids downwardly along said spillway;

pumping means for withdrawing the liquid sample and the liquid reagents from respective supply vessels and injecting the sample and reagents through their respective inlets;

pump timing means for controlling the withdrawal and injection of sample and liquid reagents by said pumping means and operable in a plurality of discrete time periods within a test cycle including a first time period and a second time period subsequent to said first time period;

said pump timing means being operable during said first and second time periods to control said pumping means to substantially continuously inject liquid reagents at a substantially uniform rate into said reactor chamber;

said pump timing means being operable during said second time period to control said pumping means to substantially continuously inject liquid sample into said reactor at a substantially uniform rate, thereby enabling spectrometer analyses during said first and second time periods to provide indications of the amount of the element of interest contained in the liquid reagents and the amount of the element of interest contained in both the reagents and the liquid sample, respectively;

said reactor chamber being tubular and having a funnel shaped lower section, said first outlet being located adjacent the top of said tubular chamber, the apex of said funnel section terminating in a second outlet for draining liquid waste from said reactor chamber, means coupled and responsive to said pump timing means for draining liquid waste from said reactor chamber between the completion of said second time period and the beginning of the first time period of the next following test cycle.

2. The system according to claim 1 further including a fourth inlet to said chamber for admitting an inert gas, means in said chamber for directing the injected liquids for flow in a first direction, said fourth inlet being in position in said chamber to admit gas into said chamber for flow in a second direction substantially opposite to said first direction to carry the gas from the liquid sample countercurrent to the direction of the liquids flow and toward the spectrometer, said pump timing means comprising a motor, a rotatable cam shaft coupled to said motor, and a plurality of cams connected to said cam shaft, said pumping means including a piston and cylinder for pumping each of the liquid reagents and liqud sample, each of said cams being configured and positioned on said shaft to actuate a corresponding piston for withdrawing and injecting appropriate quantities of the respective liquids.

3. The system according to claim 2 further including additional pumping means for injecting an additional reagent into said chamber during pre-selected time periods of said test cycle.

4. An automatic system for generating gaseous samples from liquid samples and reagents and for transferring gaseous samples for measurements in an atomic absorption spectrometer, said system comprising:

means defining a reaction chamber having a first outlet in communication with an absorption spectrometer measuring cuvette and first, second, and third inlets for injecting liquid samples and first and second liquid reagents respectively into said chamber;

pumping means for withdrawing the liquid sample and the liquid reagents from respective supply vessels and injecting the sample and reagents through their respective inlets;

said system further including a fourth inlet to said chamber for admitting an inert gas, means adjacent the internal surface of the wall of said chamber for directing the injected liquids for flow in a first direction, said fourth inlet being positioned in said chamber to admit gas into said chamber for flow in a second direction substantially opposite to said first direction to carry the gas from the liquid sample countercurrent to the direction of the liquids flow and toward the spectrometer;

pump timing means for controlling the withdrawal and injection of sample and liquid reagents by said pumping means and operable in a plurality of discrete time periods within a test cycle including a first time period and a second time period subsequent to said first time period;

said pump timing means being operable during said first and second time periods to control said pumping means to substantially continuously inject liquid reagents at a substantially uniform rate into said reactor chamber;

said pump timing means being operable during said second time period to control said pumping means to substantially continuously inject liquid sample into said reactor at a substantially uniform rate, thereby enabling spectrometer analyses during said first and second time periods to provide indications of the amount of the element of interest contained in the liquid reagents and the amount of the element of interest contained in both the reagents and the liquid sample, respectively.

5. The system according to claim 4 wherein said pumping means includes means for withdrawing liquid sample from the liquid sample supply vessel during said first period and discharging the liquid sample drawn from the latter supply vessel into said reactor chamber during said second time period for combination with the reagents to form a gaseous sample.

6. The system according to claim 5 wherein said withdrawing means includes a movable withdrawal conduit, and means responsive to said pump timing means for automatically inserting said conduit into the liquid sample vessel.

7. The system according to claim 6 including a turntable for supporting a plurality of sample supply vessels, a movable table for supporting a flushing fluid supply vessel, said turntable being rotatably coupled to said movable table, means interconnecting said turntable and said movable table on the one hand and said pump timing means on the other hand for rotating said turntable and moving said table under control of said pump timing means to align said withdrawal conduit with the liquid sample vessel during the first time period and to align said withdrawal conduit with the flushing supply vessel during a period of said test cycle subsequent to said first and second time periods.

8. The system according to claim 4 including a wash liquid reservoir, a wash liquid receptacle having a surrounding container for collecting overflow from the wash liquid receptacle, a wash liquid supply conduit for communicating wash liquid from said wash liquid reservoir to said wash liquid receptacle, pump means for pumping wash liquid from said wash liquid reservoir to said wash liqud receptacle, said wash liquid receptacle haivng an overflow collecting chamber, means for draining the injected liquid from said chamber, and an overflow conduit coupling said container and said drain means.

9. The system according to claim 8 including means for controlling said drain means to prevent the discharge of water liquid from said reaction chamber during said first and second time periods and to enable reaction mixture to flow from said chamber during the time period remaining in each measuring cycle subsequent to said first and second time periods.

10. The apparatus according to claim 4 including a reservoir for containing an addition liquid, a fifth inlet to the reaction chamber, a supply conduit coupling said addition liquid reservoir and said fifth inlet to the reactor chamber for supplying addition liquid to said chamber, and means for controlling the supply of the addition liquid to said reactor chamber at a time period prior to said first and second time periods in each measuring cycle.

11. The apparatus according to claim 4 wherein the pump timing control means comprises a synchronous motor and a cam shaft driven thereby, said cam shaft including a plurality of control cams drivingly connected to said pumping means, sample taking means including a withdrawal tube removable into and out of the sample supply vessel, an additional control cam carried by said cam shaft and drivingly connected to said sample taking means, the time of revolution of said cam shaft being equal to the duration of one measuring cycle.

12. The system according to claim 4 including a reservoir for containing a blank liquid free of the element to be determined, a conduit coupling said blank liquid reservoir and said chamber one to the other for conveying the blank liquid to said reaction chamber, and means for controlling the conveyance of the blank liquid to supply the blank liquid to said reactor chamber during said first time period.

13. An automated system for generating gaseous samples from liquid samples and reagents and for transferring gaseous samples for measurements in an atomic absorption spectrometer, said system comprising:

means defining a reaction having a first outlet in communication with an absorption spectrometer measuring cuvette and first, second, and third inlets for injecting liquid samples and first and second liquid reagents respectively into said chamber;

pumping means for withdrawing the liquid sample and the liquid reagents from respective supply vessels and injecting the sample and reagents through their respective inlets;

pump timing means for controlling the withdrawal and injection of sample and liquid reagents by said pumping means and operable in a plurality of discrete time periods within a test cycle including a first time period and a second time period subsequent to said first time period;

said pump timing means being operable during said first and second time periods to control said pumping means to substantially continuously inject liquid reagents at a substantially uniform rate into said reactor chamber;

said pump timing means being operable during said second time period to control said pumping means to substantially continuously inject liquid sample into said reactor at a substantially uniform rate, thereby enabling spectrometer analyses during said first and second time periods to provide indications of the amount of the element of interest contained in the liquid reagents and the amount of the element of interest contained in both the reagents and the liquid sample, respectively;

said reactor chamber being generally cylindrical and having upper and lower end portions, said first outlet being adjacent said upper portion, a second outlet located adjacent said lower portion for draining liquid waste from said reactor chamber, a fourth inlet to said chamber for admitting an inert carrier gas, means adjacent the internal surface of said cylindrical chamber for directing the injected liquid for flow in a first direction, said fourth inlet being disposed adjacent said lower portion to admit carrier gas into said chamber for flow in a second direction substantially opposite to said first direction to carry the gas from the liquid sample countercurrent to the direction of the liquids flow and towards the spectrometer, a liquid sample carrier for receiving a plurality of liquid sample vessels, a support for a wash liquid receptacle, said pumping means including a withdrawal conduit, means responsive to said timing means for locating said conduit and said sample carrier relative to one another to withdraw sample liquid from a selected liquid sample vessel during said first time period and for locating said conduit and said support relative to one another for withdrawing wash liquid from the wash liquid receptacle during the third time period of said measuring cycle, said conduit lying in communication with said first inlet, discrete supply vessels for the first and second liquid reagents respectively and conduits coupling said first and second reagent supply vessels and said second and third inlets respectively.

14. The system according to claim 13 wherein said directing means includes a helical spillway adjacent its inner surface, said spillway having a vertical side wall for receiving injected liquid and directing such liquids along said spillway in a downward direction towards said lower portion, a baffle plate extending upwardly from said helical face in lateral opposition to the sample and reagent inputs.

15. The system according to claim 13 including a source carrier gas, a supply vessel for one of the liquid reagents and having a closure member, a first conduit coupling said carrier gas source and said reagent supply vessel one to the other and a second conduit coupling said carrier gas source and said fourth inlet one to the other, a first pressure regulator in said first conduit, a second pressure regulator in said second conduit, said second conduit having a pair of branch conduits each including an adjustable flow restrictor and connected to said reaction chamber, a supply conduit coupling said reagent supply vessel and said reaction chamber one to the other, said reagent supply conduit and said first conduit extending through said closure member with said reagent supply conduit extending substantially to the bottom of said reagent supply vessel, a control valve in each of said first and second conduits with the control valve of said second conduit being disposed in one of said branch conduits, and means for controlling said valve to open and closed positions in an out-of-phase relation one to the other.

16. The system according to claim 15 including a conduit interconnecting the branch conduits of the carrier gas supply line, said interconnecting conduit including an adjustable flow restrictor and a flow meter.

* * * * *

UNITED STATES PATENT AND TRADEMARK OFFICE
CERTIFICATE OF CORRECTION

PATENT NO. : 4,230,665
DATED : October 28, 1980
INVENTOR(S) : Bernhard W. Huber

It is certified that error appears in the above—identified patent and that said Letters Patent is hereby corrected as shown below:

Column 16, line 59, "liqud" should read -- liquid --.

Column 18, line 9, "haivng" should read -- having --.

Column 18, line 8, "liqud" should read -- liquid --.

Column 18, line 15, "water" should read -- waste --.

Column 18, line 52, after "reaction" insert -- chamber --.

Signed and Sealed this

Twenth-eighth Day of September 1982

[SEAL]

Attest:

Attesting Officer

GERALD J. MOSSINGHOFF

Commissioner of Patents and Trademarks